United States Patent [19]

Nowak

[11] Patent Number: 5,244,809
[45] Date of Patent: Sep. 14, 1993

[54] DETERMINING THE CONCENTRATION OF ADDITIVES IN PETROLEUM FUELS

[75] Inventor: Anthony V. Nowak, Fullerton, Calif.

[73] Assignee: Atlantic Richfield Company, Los Angeles, Calif.

[21] Appl. No.: 968,644

[22] Filed: Oct. 29, 1992

[51] Int. Cl.[5] ............................................. G01N 35/08
[52] U.S. Cl. ........................................ 436/56; 436/60; 436/139; 436/178; 422/82.05; 422/101
[58] Field of Search ............... 436/56, 60, 178, 139; 44/59; 422/101, 82.05

[56] References Cited

U.S. PATENT DOCUMENTS

| | | | |
|---|---|---|---|
| 3,975,572 | 8/1976 | Reick | 210/94 |
| 4,009,008 | 2/1977 | Orelup | 44/59 |
| 4,084,091 | 4/1978 | Thomas | 73/61.54 |
| 4,514,503 | 4/1985 | Orelup | 436/60 |
| 4,717,671 | 1/1988 | Melpolder | 436/39 |
| 4,918,020 | 4/1990 | Nowak | 436/56 |

Primary Examiner—James C. Housel
Assistant Examiner—N. Bhat
Attorney, Agent, or Firm—Michael E. Martin

[57] ABSTRACT

The concentration of detergent additives and the like in motor gasoline and similar liquid petroleum fuels is measured by evaporating a sample of the fuel and passing the sample through a light-scattering detector to measure the concentration of unevaporated particles of high molecular-weight, low volatility material present in the additive concentrate. A gasoline sample may be passed through the detector by a transport medium comprising one of heptane and iso-octane. Photo detector signals generated by the additive-containing sample are compared with signals detected with samples not containing any additive. The sample and the transport medium are condensed after analysis. The method is fast, does not require venting of volatile hydrocarbon fluids to atmosphere and may be carried out using a minimal quantity of fuel product as the sample.

10 Claims, 1 Drawing Sheet

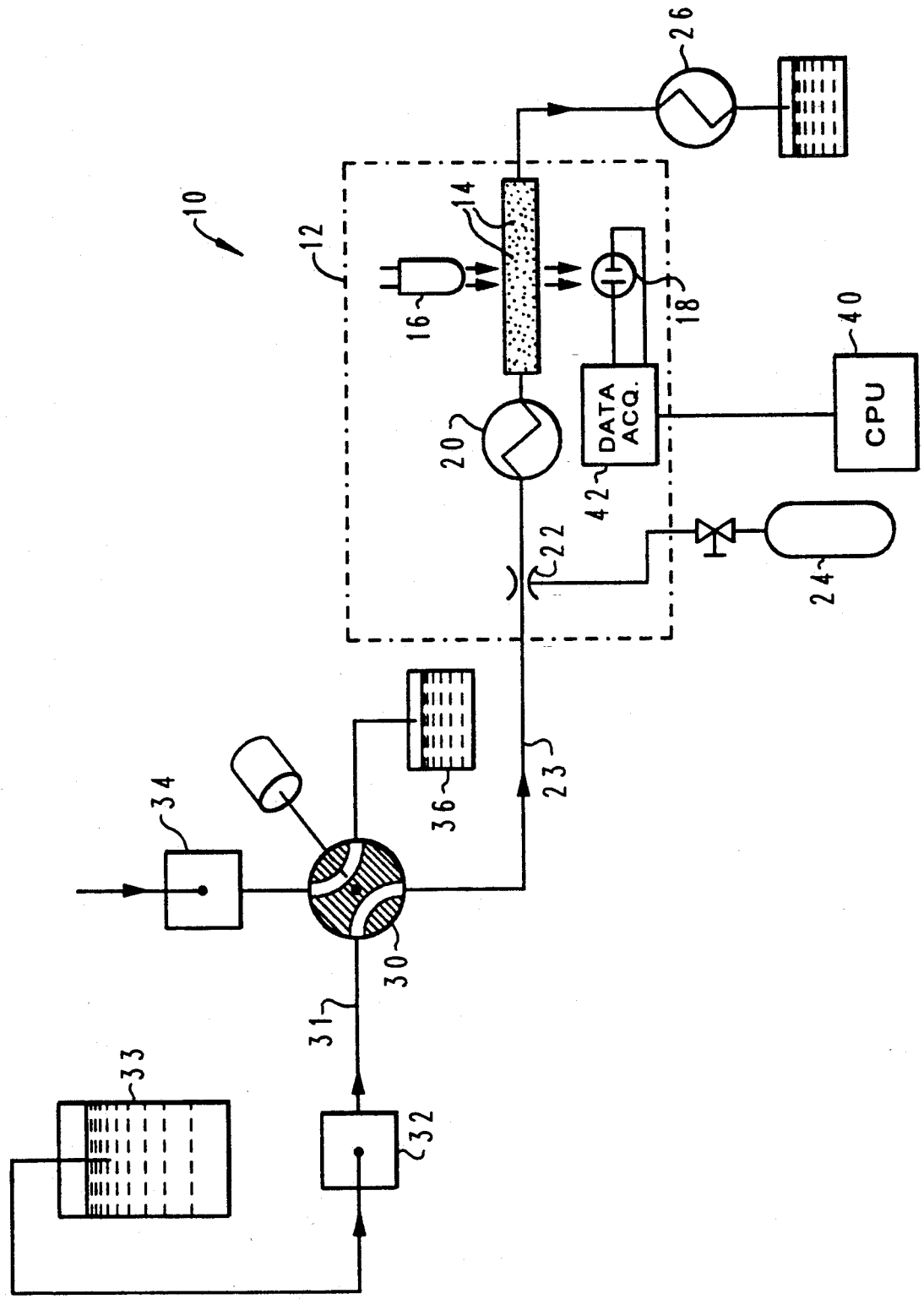

DETERMINING THE CONCENTRATION OF ADDITIVES IN PETROLEUM FUELS

BACKGROUND OF THE INVENTION

1. Field of the Invention

The present invention pertains to a method for determining the concentration of certain additives in petroleum fuels, such as detergent additives in motor gasoline, for example.

2. Background

Certain petroleum fuels, such as motor gasoline, contain additives which have detergent properties to prevent fouling of fuel injection systems of modern internal combustion engines. Detergent additives are usually formulated as concentrates made up of a mixture of specific compositions and are usually proprietary to the manufacturer. Anti-corrosion and deicing materials may also be in the additive mixture or "package". These types of additives are also usually added to bulk fuel shipments at the point of loading into transport vehicles, such as tank trucks, when such vehicles are loaded at distribution terminals. The additives are usually added to the fuel by injector devices which are controlled to inject different amounts of additive concentrate in accordance with the grade of the fuel product.

Various existing and expected future governmental regulations require certification of the amount of detergent additive in motor gasoline, for example. This regulatory certification creates a need for rapid, accurate, and uncomplicated methods for verifying the concentration of a particular additive in fuels offered for sale at service station pumps and other final distribution points.

Several methods have been developed for determining the concentration of certain additives in motor gasoline. Known methods generally depend on the detection of a particular, usually minor, component in the additive mixture which is assumed to be representative of the concentration of the additive in the fuel. My U S. Pat. 4,918,020 assigned to the assignee of the present invention pertains to a method for determining the presence of an invisible marker dye in motor gasoline which is added to the gasoline with an additive concentrate or "additive package" in the manner described above. The method of the '020 patent is attractive in that it is relatively uncomplicated, fast, accurate and requires very little equipment. However, the method described in '020 patent is not usable with motor gasolines which contain oxygenates. Since modern gasolines do or will all require the use of oxygenates, the solid-phase extraction method described in the '020 patent will not be useful for detecting the presence of detergent additive materials in such fuels.

U.S. Patent Application Ser. No. 07/825,343, filed Jan. 24, 1992, in the name of Sarkiss Zoumalan, and assigned to the assignee of the present invention, describes a method for detecting marker dye in motor gasoline which relies on the use of a gas chromatograph equipped with a selective nitrogen/phosphorous detector to separate the marker dye from other gasoline components and determine the nitrogen content of the marker dye. However, this method requires the use of relatively sophisticated and expensive equipment, and the response characteristics of the detector system and method require close monitoring.

Certain other methods have been considered including an evaporative/infrared technique which relies on the fact that the additive mixture usually contains an active nitrogen component which is active in the infrared detection range. Detection of this active nitrogen component can be related to the total additive mixture concentration in the fuel. In the described method, the fuel is evaporated under elevated temperature and vacuum conditions leaving the additive as a gummy residue. The method is relatively time consuming, requiring approximately eight and one half hours for evaporation of the fuel and analysis of the residue. Moreover, the method requires very careful dissolution of the residue using chloroform or similar solvents. Although the method has certain drawbacks, it is currently being considered by the State of California, U.S.A., as an acceptable method of gasoline-additive analysis.

The drawbacks associated with prior art methods, including those described above, have led to the development of the present invention which has numerous advantages described herein.

SUMMARY OF THE INVENTION

The present invention provides a unique method for the rapid determination of the concentration of certain additives in liquid petroleum fuels. In accordance with an important aspect of the present invention, a method is provided for determining the concentration of a detergent additive dispersed in a quantity of liquid petroleum fuel wherein the concentration of a major component of the additive mixture, comprising a relatively high molecular weight, low volatility material, is determined and is correlated with the concentration of the total additive mixture dispersed in the fuel. The component whose concentration is measured is easily separated from the fuel by evaporating a fuel sample while transporting the fuel sample through a measurement chamber and while retaining the additive component, particularly a high molecularweight, low volatility (relative to the fuel components) polymer, as particles which can be detected by means such as a light source and photodetector. In particular, a light-scattering type detector is preferably used wherein a focused light beam is scattered by the presence of the additive component particles in such a way that a signal is obtained which is related to the concentration of the particles, and correlated with the concentration of the additive mixture in the fuel sample.

In accordance with another important aspect of the present invention, a method is provided for determining the concentration of an additive in motor gasoline by subjecting a sample of the gasoline to an evaporation process to evaporate the gasoline liquid components while leaving additive materials, particularly a relatively high molecular-weight, low volatility polymer like material, in liquid form so that droplets or particles of the material are formed which may be detected by a scattered light measurement device, and the concentration of such particles may be related to the concentration of the additive in the sample. The sample is evaporated and transported through a measurement chamber, and then condensed back to liquid form in a relatively short time period and without loss of volatile fuel components.

In accordance with yet another important aspect of the present invention, a method is provided for measuring the concentration of a detergent additive mixture in motor gasoline wherein the concentration of a relatively high molecular-weight, non-volatile material is determined and is correlated with the total additive concentration.

The method of the present invention is advantageous in that it does not depend on the detection of minor components of motor fuel additives but does instead depend on the determination of a bulk property of a major component of the additive. In this way, additives which can be separated from the fuel by evaporation of the fuel components without evaporation of a major additive component yields a more accurate measurement of the concentration of the total additive mixture. The method of the present invention uses a light-scattering type detector which is relatively sensitive and can be operated at relatively low sensitivity settings to increase the signal-to-noise ratio of the measurement process.

Another advantage of the present invention is that the method may be performed in a very short period of time, can be performed on site at the distribution points of motor fuels, requires very little technical skill to perform, and uses a unique arrangement or combination of equipment which is compact and relatively uncomplicated to operate. Still further, the small sample of fuel which is required for performing the method minimizes the need for complicated equipment or storage containers, eliminates the necessity of venting volatile fuel components to atmosphere and reduces certain hazards associated with handling the fuel sample.

Those skilled in the art will recognize the above-described features and advantages of the invention as well as other superior aspects thereof upon reading the detailed description which follows in conjunction with the drawing.

BRIEF DESCRIPTION OF THE DRAWING

The drawing FIGURE is a schematic diagram of a system for practicing the method of the present invention.

DESCRIPTION OF A PREFERRED EMBODIMENT

Motor gasolines containing additive mixtures typically include as part of the additive mixture, a carrier fluid and a detergent composition as major components, combined with other components in lesser amounts which serve selected purposes. By design, these additives are thermally stable such that they can survive high temperatures in the engine combustion chambers without decomposition and, thus, are ideally suited for a dynamic evaporative process such as that which takes place in the heated drift tube of a light scattering detector.

Since the method of the present invention is non-selective, and does not depend on a specific chemical property of the individual additive components, it is not even necessary to know the chemical identity and/or composition of the additive components. In fact, chemical identity of additive components are usually carefully guarded trade secrets, and are not divulged even to additive purchasers. Often, purchasers must sign a non-analysis clause as part of the purchase agreement. The method described herein can be applied to the quantitation of additive mixtures, concentrates or "packages" chemically different. The only criterion for method applicability is that the additive components are non-volatile with respect to the hydrocarbon portions of the gasoline under the described experimental conditions, and that the detector response can be calibrated with that particular additive package. Accordingly, the fuel may be evaporated while allowing the additive component, such as a high molecular-weight polymer, for example, to form microscopic-size droplets or particles. The concentration of these particles may then be measured to determine the concentration of the additive in the fuel.

In accordance with the method of the present invention, a sample of fuel is, preferably, carried by a suitable transport medium, such as heptane or iso-octane, to means for evaporating the transport medium and the fuel leaving the relatively high molecular-weight polymer material in the additive in particle form. This sample stream is then passed before a light source by an inert gas, for example, whereupon the light source is "scattered" or reflected in accordance with the concentration of particles passing before it. A photodetector disposed relative to the light source to measure the change in "scattered" light is then operable to produce a signal which may be related to a signal generated by selected standards so that the concentration of the material in the sample swept past the light source may then be determined. Finally, the sample being analyzed and the transport medium may be recondensed and disposed of with relative ease.

The method may be carried out on relatively small samples of liquid fuel whose additive concentration is to be analyzed. Moreover, the amount of transport medium required for sample analysis may also be relatively small. As will be described further herein, motor gasoline samples as small as 5.0 microliters ($\mu$l) may be measured in accordance with the invention. The time required for analysis may be less than one minute, and the amount of transport medium required is also minor, for example, a flow rate of about 24 ml/hr. This small fluid sample and transport fluid quantity may be easily condensed thereby eliminating the requirement for any type of elaborate collection system such as would be required for other vapor phase materials and measurement processes.

Referring to FIG. 1, there is illustrated in schematic form the basic elements of a system for carrying out the method of the present invention. The system illustrated is generally designated by the numeral 10 and includes an apparatus known as an evaporative light-scattering detector generally designated by the numeral 12. The detector 12 may be of a type manufactured by Varex Corporation, Burtonsville, MD as their model ELSD-MKIIA. The schematic diagram of FIG. 1 is intended to illustrate the general principles of operation of the detector 12 and is not intended to be otherwise limiting.

Basically, the detector 12 includes means forming a chamber 14 through which a sample of the fuel to be analyzed is conducted in a vapor form, but under conditions which do not evaporate the major components of the fuel additive concentrate. At least a major component of the additive concentrate does, in fact, flow through the chamber 14 as fine particles which interrupt or obstruct light from a source 16 so that the "scattering", reflection or interruption of the light is sensed by a photodetector 18. The light source 16 may be a laser light source, for example. A heat exchanger 20 is provided in the apparatus 12 for vaporizing the fuel sample together with the transport medium. The fuel sample is propelled through the heat exchanger 20 and the chamber 14 in an atomized state as provided by a nebulizer or atomizer 22 also forming part of the apparatus 12. A controllable source 24 of inert gas, such as nitrogen, is used to atomize and propel the sample being analyzed and its transport medium through the heat exchanger 20 and the chamber 14. The sample and transport medium are then passed through a suitable condenser 26 so that essentially all of the volatile sample and its transport medium are recovered in an efficient and uncomplicated manner.

The fuel sample to be analyzed is preferably introduced to the apparatus 12 through a suitable conduit 23 operably connected to the atomizer 22, and to a motor operated valve 30 which is ported to be in communication with a source 33 of transport medium by way of a pump 32 and also in communication with a source of fuel sample such as a metering pump 34. Alternatively, a waste tank 36 may receive fluids by way of the valve 30. The metering pump 34 may, in fact, be a syringe which is used to extract the sample of fuel to be analyzed from storage tanks and the like.

Detergent additive concentrates used in motor gasolines, typically, include higher molecular weight nitrogen-containing polymer-type compositions which do not evaporate at the same or near the same temperatures as motor gasoline and such transport mediums as heptane or iso-octane. For example, an additive concentrate formerly sold by Amoco Corporation, Chicago, Illinois, known as Amoco No. 6998, and used in motor gasoline, contains a higher molecular weight carrier fluid and detergent composition which will remain in particle form at temperature conditions at which motor gasoline and transport mediums such as heptane or iso-octane will evaporate. Accordingly, applying a suitable amount of heat by way of the heat exchanger 20 to a sample of motor fuel as it is propelled through the apparatus 12, will cause all materials in the sample but the additive concentrate to be in a vapor phase when it is conducted through the chamber 14. In this way the degree of light scattering caused by the particles of a major component of the additive concentrate may be detected by the photodetector 18 and compared to gasoline samples tested without any additive concentrate to ascertain the concentration of the additive in the fuel.

The apparatus 12 may be connected to a suitable, digital computer 40 (CPU) whereby the signals generated by the photodetector 18 may be received from a suitable data acquisition and conditioning circuit 42 within the apparatus 12 so that comparative signals may be analyzed to determine the concentration of an additive in a sample of fuel. The system 10 may be calibrated by passing samples of motor gasoline or other refined petroleum liquid through the chamber 14 in a vapor phase together with the transport medium to determine the output signal of the apparatus 12 when no particulate matter is present in the chamber 14. Of course, additional samples with various known concentrations of additive concentrate added thereto may also then be passed through the chamber 14 under the controlled conditions of operation of the system 10 to correlate the output signal from the apparatus 12 with the amount of additive in the fuel sample. In this way a calibration curve or table may be established from which readings taken from measurement of fuel samples may be compared so that the actual concentration of additive in a fuel sample may be determined.

A typical operating cycle of the system 10 will now be described. After each sample measurement, the apparatus 12 is "purged" of sample fuel by positioning the valve 30 in the position shown and pumping a suitable quantity of transport medium through the nebulizer 22, the heat exchanger 20, the chamber 14, and the condenser 26 to thoroughly cleanse the apparatus 12 of additive containing fuel residue. A calibration check of the output signal of the apparatus 12 may also be made during the purge or cleansing operation. When it is desired to test a sample of fuel, such as motor gasoline, for additive concentration, the valve 30 may, of course, be rotated 90 degrees clockwise, viewing the drawing FIGURE and the sample of fuel to be measured injected into the valve 30 and the transport medium supply conduit 31 by way of the pump 34. As mentioned earlier, the pump 34 may be simply a hand-held syringe. After injecting the fuel sample into the system, the valve 30 is then rotated to the position shown in the drawing FIGURE, and a suitable quantity of transport medium is pumped with the fuel sample through valve 30, the conduit 23 and through the nebulizer 22, and the heat exchanger 20 and into the chamber 14. The transport medium and the fuel sample are evaporated under controlled temperature conditions in the heat exchanger 20, so that as the sample to be measured passes through the chamber 14 only particles of additive material, such as the detergent material and carrier, including polyisobutylene, for example, remain unevaporated. The concentration of the component in the sample is then detected by the photo-detector 18, and a signal is transmitted from the circuit 42 to the CPU 40. The material discharged from the apparatus 12 is condensed by the condenser 26 and recovered for disposal or reuse, such as by returning the sample and its transport medium to the source of the sample. The use of a compatible fluid for the transport medium is thus of some importance in field operations of the system in accordance with the method of the present invention.

In one preferred embodiment of a system 10 and method according to the invention, the system components may be as follows. The reservoir for the mobile phase or transport medium of the source 33 may be a Kontes Ultraware HPLC 500ml reservoir available from VWR Scientific. The pump 32 may be a model 590 programmable solvent delivery module available from Millipore Corp., Waters Chromatography Division, Millford, Massachusetts. The valve 30 may be a model EC6W5-- sampling valve available from Valco Instruments Company, Houston, Texas including a two position electric actuator to introduce the sample into the mobile phase or transport medium. The valve 30 may be fitted with a Valco syringe adaptor (part number ZLA-1) which enables the use of disposable plastic syringes for sample injection. Approximately 1/16 inch outside diameter by 0.007 inches inside diameter PEEK tubing and appropriate fittings from Upchurch Scientific Company, Oak Harbor, Washington may be used to interconnect all components of the system. The gas used in the nebulizer 22 is preferably pure, inert, dry carrier gas such as nitrogen at 80 psig from the cylinder 24. The system 10 may be connected such that the pump 32 will not pump the transport medium through the detector apparatus 12 unless a specified minimum amount of nitrogen is flowing through the system. For experimental or test purposes, a small glass bottle set in a beaker partially filled with ice may be used as the condenser 26. The data acquisition module and CPU may comprise a Perkin Elmer model 1020 Personal Integrator to acquire and process data from the detector 12.

The overall tubing length between the pump 32 and the apparatus 12 is preferably on the order of about 100 cm to provide a time delay such that adequate sample diffusion occurs in the conduit path 31, 23 before the sample reaches the apparatus 12. Since a relatively large sample volume is used, this tubing length spreads out the sample "slug" so that it does not overwhelm the response capacity of the detector apparatus. Such an arrangement also results in a smoother response signal and operation of the data acquisition system. It is important that the detector apparatus 12 be situated such that the sample freely exits the apparatus and cannot collect in the apparatus flow path.

In carrying out a calibration procedure, sample analysis and data processing, a preferred procedure is as follows. The reservoir or source 33 is filled with an appropriate amount of chromatography-grade heptane or iso octane. The pump 32 is energized but will not be activated if it is properly connected to the apparatus 12 since a preferred arrangement does not allow operation of the pump 32 until gas is flowing to the nebulizer or venturi 22. Correct priming of the pump should be given due attention. By way of example, the pump flow rate may be set at 0.4 ml/min. This flow rate is optimized to produce a smooth response signal from the apparatus 12 while resulting in a total effluent output from the pump of only 24.0 ml/hour. With power applied to the motor of the injection valve 30, gas flow to the apparatus 12 may be commenced at a rate that produces a numerical indication of about 40 mm. on the apparatus indicator. The apparatus temperature is preferably set at about 150° C. in the chamber 14. Once the apparatus is set up and properly calibrated, it should only be necessary to turn on power to the apparatus 12, and the valve 30 and activate the source of gas for the nebulizer 22 and wait for the system to equilibrate in order to be ready to analyze fuel samples.

A series of standard solutions of samples is prepared which are known to contain certain amounts of additive materials covering the expected range of concentrations of additive normally present in motor gasolines, for example. Since it is known that an inherent property of light scattering detectors is that the response signal is non-linear with respect to the concentration of the measured particles, regardless of the composition, it is important that the entire range of additive concentrations be represented in a series of calibration solutions used to produce a calibration curve. Regular grades of gasoline are usually treated at a lower level of additives of the type discussed herein than premium gasoline grades. Additive concentrations for one brand of "regular" gasoline typically range from 0.6% to 0.8% by volume, whereas for the same brand of "premium" gasoline, the additive concentration may range from 0.8% to 1.2% by volume.

A 2% v/v stock solution is prepared by dissolving 2.00ml of the additive concentrate with "unadditized" gasoline up to 100ml. The calibration standards are prepared by taking known volumes of the stock solution and diluting with unadditized gasoline. For example, 5.0 ml of the stock solution would produce a 0.10% by volume standard when diluted with 100 ml of unadditized gasoline. Six "standards" of 0.00, 0.25, 0.50, 0.75, 1.00, and 1.25 percent by volume additive samples are then prepared and run through the analysis procedure. It is possible to complete four individual measurements within a one minute period and it is advantageous to make replicate measurements of the same sample for improved analysis statistics.

In practice, it is advantageous to use disposable syringes as the source of sample or as the pump 34, for example. It is important to ensure that no air bubbles or other contaminants are contained in the sample volume to cause spurious detector response.

Actual samples of fuel for analysis are analyzed in generally the same manner as described above for general operation of the system 10 and as used in the calibration procedure. With the system 10 in operation and equilibrated, it is only necessary to inject samples into the valve 30 and actuate an injection switch after first assuring that the data acquisition system is ready.

As will be appreciated from the foregoing description, a rapid and unique measurement process is provided which determines the concentration of additive in a sample of motor gasoline. The time required for the measurement process as well as the quantity of volatile fluids required to be handled are minimal.

Although a preferred embodiment of a method and system in accordance with the present invention have been described in detail herein, those skilled in the art will recognize that various substitutions and modifications may be made without departing from the scope and spirit of the invention as recited in the appended claims.

What is claimed is:

1. A method for determining the concentration of detergent additive in motor gasoline comprising the steps of:
    obtaining a sample of motor gasoline with an unknown quantity of detergent additive disposed therein;
    evaporating the gasoline without evaporating at least a major component of the additive;
    transporting the evaporated gasoline and the unevaporated additive component through means for generating a signal responsive to the concentration of particles of said additive component as determined by a photo detector to determine the concentration of said additive in said gasoline.

2. The method set forth in claim 1 including the step of:
    transporting said sample of gasoline through said means for generating said signal with a transport medium which will evaporate at conditions which will also evaporate said sample of gasoline.

3. The method set forth in claim 2 wherein:
    said transport medium is provided as at least one of heptane and iso-octane.

4. The method set forth in claim 1 wherein:
    the concentration of said additive in said gasoline is determined by measuring the concentration of particles of a relatively high molecular weight polymer in said additive.

5. The method set forth in claim 1 including the step of:
    condensing said sample of gasoline after subjecting said sample of gasoline to measurement by said means.

6. A method for determining the concentration of a detergent additive in motor gasoline comprising the steps of:
    providing a system for measuring the concentration of said additive comprising a source of a transport medium, a light-scattering detector, including means for evaporating a sample of said gasoline to be measured, condenser means for condensing said sample, and valve means for selectively communicating said sample with said detector and said source of transport medium;

placing said valve means in communication with a source of said sample;

placing said valve means in communication with a source of said transport medium and said detector;

causing said transport medium to transport said sample to said detector and evaporating said transport medium and gasoline in said sample without evaporating at least a major component of said additive;

passing said evaporated sample and said evaporated transport medium through said detector while measuring the relative concentration of at least one of said components in said additive by detecting the quantity of unevaporated particles of said component entrained with said gasoline and said transport medium in vapor form; and recovering said sample of gasoline and a quantity of said transport medium which has been passed through said detector.

7. The method set forth in Claim 6, including the step of:

comparing a signal generated by said detector as a result of passing said sample of gasoline with said additive therein through said detector with a signal generated by said detector in the presence of a sample of gasoline without said additive therein to determine the concentration of said additive in said sample of gasoline.

8. The method set forth in Claim 6 wherein: said sample and said transport medium are recovered by condensing said sample and said transport medium.

9. A system for measuring the concentration of an additive in a liquid petroleum fuel comprising:

a light scattering detector including means forming a chamber for passing a sample of said fuel therethrough in vapor phase with unevaporated particles of additive entrained in said vapor phase;

photo detector means responsive to the concentration of particles in said chamber to provide a signal related to said concentration of particles;

means for evaporating said sample of fuel;

a source of a transport medium for transporting a sample of fuel to said chamber;

valve means interposed between said source of transport medium and said chamber and operable to receive a sample of fuel with a quantity of said transport medium for transporting said sample of fuel to said chamber;

a pump for pumping said transport medium and said sample of fuel to said chamber; and means for recovering said sample of fuel and said transport medium without venting said sample or said transport medium to atmosphere.

10. The system set forth in claim 9 wherein:

said means for recovering comprises a condenser for receiving said sample of fuel and a quantity of said transport medium and condensing said sample and said quantity.

* * * * *